CHRYSANTHEMUM PLANT
Filed March 7, 1973
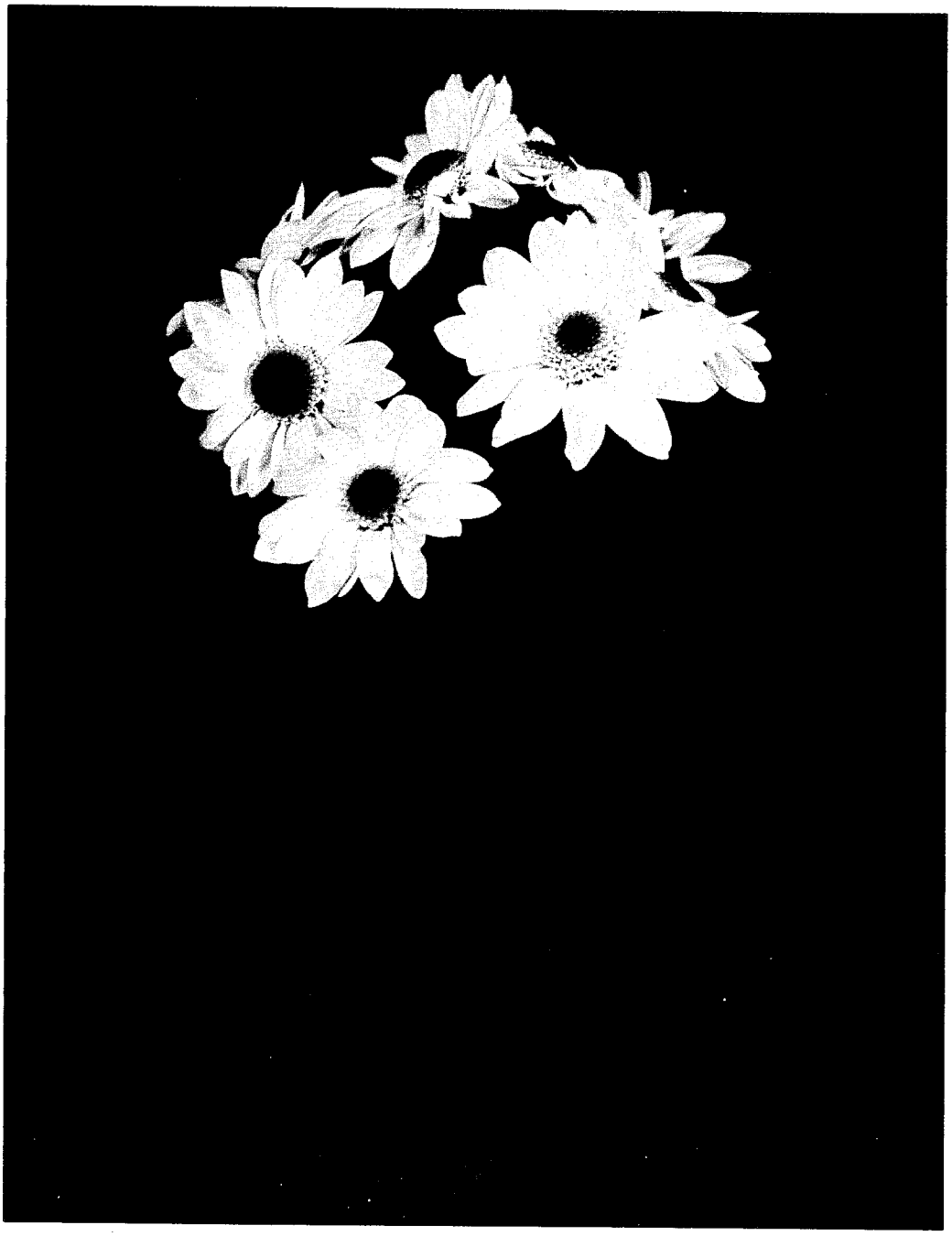

United States Patent Office

Plant Pat. 3,597

Patented Aug. 20, 1974

3,597
CHRYSANTHEMUM PLANT

Walter H. Jessel, Jr., Doylestown, and William E. Duffett, Akron, Ohio, assignors to Yoder Brothers, Inc., Barberton, Ohio

Filed Mar. 7, 1973, Ser. No. 338,851

Int. Cl. A01h *5/00*

U.S. Cl. Plt.—74 1 Claim

The present invention comprises a new and distinct cultivar of chrysanthemum plant known by the varietal name Pride which is a seedling of #67100–55 × Dramatic. One parent is unpatented and identified for breeding purposes by the indicated breeding number. The cultivar Dramatic is disclosed and claimed in U.S. Plant Pat. 3,189.

The new cultivar is similar to the unpatented cultivar Yellow Bonnie Jean and the cultivar Improved Yellow Bonnie Jean, disclosed in the copending application Ser. No. 170,936, filed Aug. 11, 1971, in the name of Helmut Karl Gortz, in that the new cultivar is a yellow daisy cultivar suitable for pot mum culture.

The new cultivar is distinguished from Yellow Bonnie Jean and Improved Yellow Bonnie Jean by the following characteristics when grown under comparable conditions:

1. A year round recommended flowering period as a spray pot. Yellow Bonnie Jean and Improved Yellow Bonnie Jean are suitable as spray pots only during high light periods of the year.

2. A true single daisy flower form, quite formal in appearance, compared to the more informal duplex daisy form of Yellow Bonnie Jean and Improved Yellow Bonnie Jean.

3. Its flowers are approximately ¾″ smaller in diameter.

4. A much darker, more intense yellow flower color with little or no fading. Yellow Bonnie Jean fades quickly and extensively as the flower matures, particularly in high light, high temperature periods. Improved Yellow Bonnie Jean has better color retention than Yellow Bonnie Jean, but it also fades. Compared to Pride, its color at the marketing stage and at maturity is still considerably lighter.

5. An improved pot mum habit, including 6″ to 8″ less vigor, 6″ more spread, and a far better response to present day growth regulators. Due to its shorter habit, the new cultivar is recommended for pot mum culture only, and not for flower spray programs like Bonnie Jean and Improved Yellow Bonnie Jean.

6. Increased keeping quality of 7–13 days under home conditions as a spray pot.

7. A foliage less sensitive to injury from applications of present day greenhouse insecticides.

8. Smoother textured foliage with reduced prominence in venation.

9. Smaller foliage; 2¾″ shorter in length, and 2¼″ narrower in width.

10. A more coarse serration of the leaf margin.

11. Improved low temperature tolerance. Pride will initiate and develop flower buds at 54°–56° F. better than Yellow Bonnie Jean and Improved Yellow Bonnie Jean.

12. Less prominent stipules.

13. Absence of pollen in the flowers. Yellow Bonnie Jean and Improved Yellow Bonnie Jean have abundant pollen which reduces keeping quality.

14. One week earlier response (9 week vs. 10 week) as a spray pot.

15. A consistent 9 week response which varies little throughout the seasons. It does not develop much of an accelerated response in spring and fall, and little heat delay in summer.

16. Medium treatment rather than tall treatment for long day week timing, due to its shorter habit.

The new cultivar was selected from the progeny of the designated parent and when asexually reproduced by cuttings at Barberton, Ohio, has been found to retain its distinctive characteristics through successive propagations.

Our new cultivar when grown in the vicinity of Barberton, Ohio, has a response period of approximately nine weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern, western, southeastern and southwestern United States, and coastal California is from January through December; in southern Florida, December through April.

The accompanying drawing shows the unique characteristics of the new cultivar, the color being as nearly true as possible with color illustrations of this type.

In the description which follows, color references are made to the Munsell Color Book, 1963 edition, and comparisons are made with the cultivars Yellow Bonnie Jean and Improved Yellow Bonnie Jean. Where only a single value or description appears for the new cultivar, the same value or comparison applies as well to the comparison cultivars.

Botanical classification: *Chrysanthemum morifolium*

| | Pride | Yellow Bonnie Jean | Improved Yellow Bonnie Jean |
|---|---|---|---|
| Bloom: | | | |
| Size | 2¼″ | 3″ | 3″. |
| Fully expanded | 2¾″ | 3½″ | 3½″. |
| Borne | Clusters on elongated pedicels | | |
| Stems | Strong and wiry | Short and strong | Short and strong. |
| Form | Daisy (single) | Daisy (duplex) | Daisy (duplex). |
| Permanence | 14–20 days | 7 days | 10 days. |
| Color: | | | |
| Center of flower | Yellow-green, 2.5GY6/10 to yellow, 7.5Y8.5/10. | Light green, 2.5GY6/8 to light yellow, 10Y8.5/10. | Light green, 2.5GY6/8 to light yellow green, 10Y8.5/10. |
| Base of petal | Yellow-green, 2.5GY7/10 | Yellow, 7.5Y8.5/8 to light yellow, 7.5Y9/4. | Yellow, 7.5Y8.5/10 to yellow, 7.5Y8.5/8. |
| Inside of petals | Dark yellow, 6.25Y8.5/12 to yellow, 7.5Y8.5/10. | Yellow, 7.5Y8.5/10 to light yellow, 7.5Y9/4. | Do. |
| Reverse of petals | Yellow, 7.5Y8.5/10 to light yellow, 7.5Y8.5/8. | Light yellow, 7.5Y9/4 to very pale yellow, 7.5Y9/2. | Light yellow, 7.5Y9/6 to light yellow, 7.5Y9/4. |
| Tonality from a distance. | Yellow | Light yellow | Yellow. |
| Discoloration | Yellow, 7.5Y8.5/10. | Light yellow, 7.5Y9/4. | Yellow, 7.5Y9.5/8. |
| Petals: | | | |
| Texture | Smooth | | |
| Appearance and form | Open at base, multi-ridged keel, tapering to a 2-notched tip. | Open at base, broadens quickly with slight longitudinal roll, broad shallow keel, tapering to a blunt tip. | Open at base, broadens quickly with slight longitudinal roll, broad shallow keel, tapering to a blunt tip. |
| Arrangement | Composite, whorled on a single receptacle. | | |
| Persistence | Resist shatter | | |
| Fragrance | Typical chrysanthemum | | |

TABLE—Continued

Botanical classification: *Chrysanthemum morifolium*

| | Pride | Yellow Bonnie Jean | Improved Yellow Bonnie Jean |
|---|---|---|---|
| Reproductive organs: | | | |
| Stamen, anthers | 200 or more | 200 or more | 150 to 200. |
| Pollen | Slight to none (functional sterility) | Excessive to none (functional sterility) | None to abundant (functional sterility). |
| Arrangement | Cluster in center of flower, if present | | |
| Styles | Present both ray and disc florets | | |
| Length | Short | | |
| Ovaries | At the base of petal attached to receptacle. | | |
| Plant: | | | |
| Form | Herbaceous | | |
| Growth | Semi-spreading | Upright | Upright. |
| Height | Approximately 10″–12″ when grown in a 5-cutting, 6″ pinched pot, grown as a spray pot and given 9 week medium treatment as defined in the timetables of Yoder Brothers, Inc., Barberton, Ohio, for the various seasons of the year. | Approximately 16″–18″ when grown in a 5-cutting, 6″ pinched pot, grown as a spray pot and given 10 week tall treatment as defined in the timetables of Yoder Brothers, Inc., Barberton, Ohio, for the various seasons of the year. | Approximately 18″–20″ when grown in a 5-cutting, 6″ pinched pot, grown as a spray pot and given 10 week tall treatment as defined in the timetables of Yoder Brothers, Inc., Barberton, Ohio, for the various seasons of the year. |
| Spread | Approximately 16″–18″ when grown in a 5-cutting, 6″ pinched pot, grown as a spray pot given 9 week medium treatment as defined in the timetables of Yoder Brothers, Inc., Barberton, Ohio, for the various seasons of the year. | Approximately 10″–12″ when grown in a 5-cutting, 6″ pinched pot, grown as a spray pot, given 10 week tall treatment as defined in the timetables of Yoder Brothers, Inc., Barberton, Ohio, for the various seasons of the year. | Approximately 10″–12″ when grown in a 5-cutting, 6″ pinched pot, grown as a spray pot, given 10 week tall treatment as defined in the timetables of Yoder Brothers, Inc., Barberton, Ohio, for the various seasons of the year. |
| Foliage: | | | |
| Top side | Dark green, 7.5GY3/4 | | |
| Size | 3¼″ long, 1¾″ wide | 6″ long, 4″ wide | 6″ long, 4″ wide. |
| Quantity | Numerous | | |
| Shape | Spatulate lobed | | |
| Texture | Smooth | | |
| Ribs and veins | Moderately prominent | Very prominent | Very prominent. |
| Edge | Moderately indented | Deeply indented | Deeply indented. |
| Serration | Coarse | Moderate | Moderate. |
| Under side | Light green, 7.5GY5/4 | | |
| Stipules | Rudimentary | Prominent | Prominent. |

We claim:

1. A new and distinct cultivar of chrysanthemum characterized particularly as to its uniqueness when compared to the cultivars Improved Yellow Bonnie Jean and Yellow Bonnie Jean by its year round recommended flowering period as a spray pot; its true single daisy flower form, quite formal in appearance; its flowers which are approximately ¾″ smaller in diameter and of a much darker, more intense yellow flower color with little or no fading; its improved pot mum habit, including 6″ to 8″ less vigor, 6″ more spread, and a far better response to present day growth regulators; its increased keeping quality of 7–13 days under home conditions as a spray pot; its foliage which is less sensitive to injury from applications of present day greenhouse insecticides, smoother with reduced prominence in venation and a more coarse serration of the leaf margin, and which is smaller, being 2¾″ shorter in length, and 2¼″ narrower in width; its improved low temperature tolerance, initiating and developing flower buds better at 54°–56° F.; its less prominent stipules, and absence of pollen in the flowers, which increases the keeping quality; its one week earlier response as a spray pot, having a consistent 9 week response which varies little throughout the seasons, and by its medium treatment rather than tall treatment for long day week timing, due to its shorter habit.

No references cited.

ROBERT E. BAGWILL, Primary Examiner